(12) United States Patent
Marton et al.

(10) Patent No.: US 11,760,974 B2
(45) Date of Patent: Sep. 19, 2023

(54) PERSONALIZED 3D NEURAL CULTURE SYSTEM FOR GENERATING HUMAN OLIGODENDROCYTES AND STUDYING MYELINATION IN VITRO

(71) Applicant: The Board of Trustees of the Leland Stanford Junior University, Stanford, CA (US)

(72) Inventors: Rebecca Marton, Stanford, CA (US); Sergiu P. Pasca, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 417 days.

(21) Appl. No.: 15/953,197

(22) Filed: Apr. 13, 2018

(65) Prior Publication Data

US 2018/0298333 A1 Oct. 18, 2018

Related U.S. Application Data

(60) Provisional application No. 62/485,251, filed on Apr. 13, 2017.

(51) Int. Cl.
*C12N 5/00* (2006.01)
*A61P 25/00* (2006.01)
*C12N 5/079* (2010.01)
*G01N 33/50* (2006.01)
*C12N 5/074* (2010.01)

(52) U.S. Cl.
CPC ......... *C12N 5/0622* (2013.01); *C12N 5/0607* (2013.01); *C12N 5/0696* (2013.01); *G01N 33/5026* (2013.01); *G01N 33/5032* (2013.01); *G01N 33/5058* (2013.01); *C12N 2500/38* (2013.01); *C12N 2501/01* (2013.01); *C12N 2501/105* (2013.01); *C12N 2501/11* (2013.01); *C12N 2501/115* (2013.01); *C12N 2501/12* (2013.01); *C12N 2501/13* (2013.01); *C12N 2501/135* (2013.01); *C12N 2501/33* (2013.01); *C12N 2501/385* (2013.01); *C12N 2501/395* (2013.01); *C12N 2501/415* (2013.01); *C12N 2501/727* (2013.01); *C12N 2501/999* (2013.01); *C12N 2506/03* (2013.01); *C12N 2506/1346* (2013.01); *C12N 2506/45* (2013.01); *C12N 2513/00* (2013.01); *C12N 2533/52* (2013.01)

(58) Field of Classification Search
None
See application file for complete search history.

(56) References Cited

U.S. PATENT DOCUMENTS

| | | | | |
|---|---|---|---|---|
| 10,494,602 | B1 * | 12/2019 | Sloan | G01N 33/5058 |
| 2007/0025975 | A1 * | 2/2007 | Anderson | C12N 5/0622 |
| | | | | 435/368 |
| 2009/0232779 | A1 | 9/2009 | Keirstead | |
| 2014/0038949 | A1 * | 2/2014 | Schultz | A61K 31/46 |
| | | | | 514/225.8 |
| 2016/0059203 | A1 | 3/2016 | Petcavich | |
| 2017/0002324 | A1 | 1/2017 | Petcavich | |
| 2017/0166857 | A1 | 6/2017 | Petcavich | |
| 2017/0322194 | A1 | 11/2017 | Petcavich | |
| 2018/0113118 | A1 | 4/2018 | Petcavich | |

FOREIGN PATENT DOCUMENTS

| | | |
|---|---|---|
| WO | 2008/013918 A2 | 1/2008 |
| WO | 2009/018587 A2 | 2/2009 |
| WO | 2010/108126 A2 | 9/2010 |
| WO | 2011/094738 A1 | 8/2011 |

OTHER PUBLICATIONS

Hoffman et al. (Nat Biotechnol. 23:699-708, 2005).*
Lundqvist et al (Toxicol in vitro 27: 1565-1569, 2013).*
Schuldiner et al. (PNAS, 97:11307-11312, 2000).*
Pasca et al (Nat Methods 12: 671-678, 2015).*
Wang et al (Neurochem Res 41: 3289-3299, 2016).*
McMorris et al (PNAS 83: 822-826, 1986).*
Neman et al (Dev Neurobiol 72: 777-788, 2012.*
Langseth et al (J Neurosc 30: 13367-13372, 2010).*
Douvaras et al. (Stem Cell Rep 3: 250-259, 2014).*
McDonnell et al (J Neur Sc 165: 77-83, 1999).*
Goldman et al (Development 142: 3983-3995, 2015).*
Piao et al Cell Stem Cell 16: 198-210 (1-27), 2015).*
Adler EM (Sc Signaling 2: ec326 (1-2), 2009).*
McComish et al (Phil Trans B 373: 1-15, 2018).*
Pamies et al (Altex 34: 362-376, Epub: Nov. 24, 2016).*
Bian et al., "Sequential Differentiation of Embryonic Stem Cells into Neural Epithelial-Like Stem Cells and Oligodendrocyte Progenitor Cells", PLoS One, May 18, 2016, pp. 1-15, 11(5):e0155227, PLoS One, San Francisco, CA.
Chen et al., "Schwann cells induce Proliferation and Migration of Oligodendrocyte Precursor Cells Through Secretion of PDGF-AA and FGF-2", J Mol Neurosci., Aug. 2015, pp. 999-1008, vol. 56, Issue 4, tion, Neurochem Res., Dec. 2016, pp. 3289-3299, vol. 41, Issue 12, Springer, Berlin, Germany.
Huangfu et al., "Induction of pluripotent stem cells from primary human fibroblasts with only Oct4 and Sox2", Nature Biotechnology, Nov. 2008, pp. 1269-1275, vol. 26, No. 11, Macmillan Publishers Limited, Basingstoke, United Kingdom.
Kim et al., "Generation of Human Induced Pluripotent Stem Cells by Direct Delivery of Reprogramming Proteins", Cell Stem Cell, Jun. 5, 2009, pp. 472-476, Elsevier, New York City, NY.

(Continued)

*Primary Examiner* — Gregory S Emch
*Assistant Examiner* — Aditi Dutt
(74) *Attorney, Agent, or Firm* — Pamela J. Sherwood; Bozicevic, Field & Francis LLP (57) ABSTRACT

Human pluripotent stem cells are differentiated in vitro into oligodendro-spheroids comprising oligodendrocytes for use in analysis, screening programs, and the like.

16 Claims, 1 Drawing Sheet
(1 of 1 Drawing Sheet(s) Filed in Color)

(56) References Cited

OTHER PUBLICATIONS

Li et al., "Generation of Rat and Human Induced Pluripotent Stem Cells by Combining Genetic Reprogramming and Chemical Inhibitors", Cell Stem Cell, Jan. 9, 2009, pp. 16-19, vol. 4, Issue 1, Elsevier, New York City, NY.
Park et al., "Reprogramming of human somatic cells to pluripotency with defined factors", Nature, Jan. 10, 2008, pp. 141-146, 451, Macmillan Publishers Limited, Basingstoke, United Kingdom.
Porcu et al., "Clobetasol and Halcinonide Act as Smoothened Agonists to Promote Myelin Gene Expression and RxRγ Receptor Activation", PLoS One, Dec. 10, 2015, pp. 1-22, 10(12),e0144550, PLoS One, San Francisco, CA.
Soldner et al., "Parkinson's Disease Patient-Derived Induced Pluripotent Stem Cells Free of Viral Reprogramming Factors", Cell, Mar. 6, 2009, pp. 964-977, vol. 136, Issue 5, Elsevier, New York City, NY.
Takahashi et al., "Induction of Pluripotent Stem Cells from Adult Human Fibroblasts by Defined Factors", Cell, Nov. 30, 2007, pp. 861-872, vol. 131, Issue 5, Elsevier, New York City, NY.
Wang et al., "High purity of human oligodendrocyte progenitor cells obtained from neural stem cells: suitable for clinical application", J Neurosci Methods, Jan. 30, 2015, pp. 61-66, vol. 240, Elsevier, New York City, NY.
Wang et al., "Role of Sonic Hedgehog Signaling in Oligodendrocyte Differentiation", Neurochem Res., Dec. 2016, pp. 3289-3299, vol. 41, Issue 12, Springer, Berlin, Germany.
Yu et al., "Induced Pluripotent Stem Cell Lines Derived from Human Somatic Cells", Science, Dec. 21, 2007, pp. 1917-1920, vol. 318, Issue 5858, vol. 4, Issue 6, American Association for the Advancement of Science, Washington, D.C.
Patani et al., "Experimental and Therapeutic Opportunities for Stem Cells in Multiple Sclerosis", International Journal of Molecular Sciences, Nov. 8, 2012, pp. 14470-14491, vol. 13, MDPI, Basel, Switzerland.
Goldman et al. (2015) "How to make an oligodendrocyte" *Development*, vol. 142, No. 23, pp. 3983-3995.
Nevin et al. "Modeling the Mutational and Phenotypic Landscapes of Pelizaeus-Merzbacher Disease with Human iPSC-Derived Oligodendrocytes" *Am J Hum Genet*, Mar. 30, 2017, vol. 100, No. 4, pp. 617-634.
Pasca et al. "Functional cortical neurons and astrocytes from human pluripotent stem cells in 3D culture". *Nat Methods*, May 25, 2015, vol. 12, No. 7, pp. 671-678.
Wang et al. (2013) "Human iPSC-derived oligodendrocyte progenitor cells can myelinate and rescue a mouse model of congenital hypomyelination". *Cell Stem Cell*, Feb. 7, 2013, vol. 12, No. 2, pp. 252-264.
Zhang et al. (2016) "Neural Subtype Specification From Human Pluripotent Stem Cells". Cell Stem Cell, vol. 19, No. 5, pp. 573-586.
Douvaras et al. (2015) "Generation and isolation of oligodendrocyte progenitor cells from human pluripotent stem cells", Nature Protocols, GB, vol. 10, No. 8, doi:10.1038/nprot.2015.075, ISSN 1754-2189, pp. 1143-1154.

\* cited by examiner

FIG. 1A FIG. 1B FIG. 1C FIG. 1D FIG. 1E FIG. 1F

PERSONALIZED 3D NEURAL CULTURE SYSTEM FOR GENERATING HUMAN OLIGODENDROCYTES AND STUDYING MYELINATION IN VITRO

CROSS REFERENCE

This application claims benefit of U.S. Provisional Patent Application No. 62/485,251, filed Apr. 13, 2017, which application is incorporated herein by reference in its entirety.

FEDERALLY SPONSORED RESEARCH AND DEVELOPMENT

This invention was made with Government support under contract MH107800 awarded by the National Institutes of Health. The Government has certain rights in the invention.

BACKGROUND OF THE INVENTION

Progress in understanding the intricate development of the human central nervous system and elucidating the mechanisms of neurological and psychiatric disorders in patients has been greatly limited by restricted access to functional human brain tissue. While studies in rodents and other mammals have provided important insights into the fundamental principles of neural development, we know little about the cellular and molecular processes responsible for the massive expansion of the forebrain in primates, nor many of its human specific features. In recent years, a paradigm shift has been achieved in the field with the introduction of cellular reprogramming—a process during which terminally differentiated somatic cells can be converted into pluripotent stem cells, named human induced pluripotent stem cells (hiPSC). These hiPSCs can be generated from any individual and, importantly, can be directed to differentiate in vitro into all germ layer derivatives, including neural cells.

While the methods and efficiency of generating hiPSCs have been significantly improved and standardized across laboratories, the methods for deriving specific neural and glial cell types remain challenging. Over the past decade, improvements in neural specification and differentiation protocols of pluripotent stem cells in monolayer have led to the generation of a variety of cell types. Nonetheless, two-dimensional (2D) methods are unlikely to recapitulate the cytoarchitecture of the developing three-dimensional (3D) nervous system or the complexity and functionality of in vivo neural networks and circuits. Moreover, these methods are laborious and costly, have limited efficiency and give rise to relatively immature neurons.

Oligodendrocytes are glial cells in the central nervous system that play a critical role in brain function. Oligodendrocytes extend processes that wrap the axons of neurons with insulating layers, allowing for more rapid transmission of signals between neurons. Oligodendrocytes also play a supportive role by supplying neurons with trophic factors and by buffering the extracellular environment. Loss of myelination can lead to the death of neurons and impaired neural function. As a result, many human diseases are associated with a loss or reduction in myelination, such as multiple sclerosis or white vanishing matter disease.

The study of myelination in health and disease is limited by the availability of appropriate models. Rodents are commonly used as a surrogate to study aspects of human biology; however, myelination is much more extensive in human than in rodent brains. Additionally, limited availability of healthy brain samples from human patients precludes the possibility of extensively studying myelination in the human brain. In recent years, attempts have been made to generate oligodendrocytes progenitor cells (OPC) and oligodendrocytes from human embryonic and induced pluripotent stem cells (hESC, hiPSCs) for the study of myelination in vitro.

hESC and hiPSC-derived models of myelination are not only essential to the study the processes of oligodendrocyte development and myelination under normal and disease conditions, but can also be applied for pharmaceutical drug screening. These models can be used to both screen for compounds that correct specific abnormalities related to certain disease states and to test the toxicity of new therapeutic compounds and chemical substances prior to human exposure. Particularly, in the field of neurotoxicity, assays capable of assessing the impairment of neuronal or glial function are still lacking for human cells.

Therefore, the development of in vitro screening platforms that recapitulate highly functional human tissue, including myelination of neurons, is of utmost importance.

Publications. Methods to reprogram primate differentiated somatic cells to a pluripotent state include differentiated somatic cell nuclear transfer, differentiated somatic cell fusion with pluripotent stem cells and direct reprogramming to produce induced pluripotent stem cells (iPS cells) (Takahashi K, et al. (2007) Cell 131:861-872; Park I H, et al. (2008) Nature 451:141-146; Yu J, et al. (2007) Science 318:1917-1920; Kim D, et al. (2009) Cell Stem Cell 4:472-476; Soldner F, et al. (2009) Cell. 136:964-977; Huangfu D, et al. (2008) Nature Biotechnology 26:1269-1275; Li W, et al. (2009) Cell Stem Cell 4:16-19).

SUMMARY OF THE INVENTION

Compositions and methods are provided for in vitro generation of human OPCs and myelinating oligodendrocytes, which may be cultured in a 3-dimensional system with central nervous system neurons. A feature of the invention is the ability to generate OPCs and oligodendrocytes from patient samples, allowing disease-relevant generation and screening of the cells for therapeutic drugs and treatment regimens. The methods utilize induced human pluripotent stem cells (hiPSCs), which may be obtained from patient or carrier cell samples, e.g. adipocytes, keratinocytes, fibroblasts, and the like. The hiPSCs are induced to develop an ectoderm fate in vitro and subsequently differentiated into spheroids that contain oligodendrocytes—human oligodendro-spheroids (hOS), as well as neural progenitors, astrocytes and neurons. The cell populations can be isolated from the hOS, or the intact hOS can be used as a model for interacting cell populations. The hOS and cells derived therefrom may be used for transplantation, for experimental evaluation, as a source of lineage and cell specific products, and the like. In some embodiments the cell cultures are feeder-free and xeno-free.

In some embodiments of the invention, populations of purified human OPC or oligodendrocytes are provided, including without limitation disease-relevant oligodendrocytes, where the cells are differentiated from induced human pluripotent stem cells (hiPSCs). In some embodiments a panel of such in vitro derived cells are provided, where the panel includes two or more genetically different cells. In some embodiments a panel of such cells are provided, where the cells can be subjected to a plurality of candidate agents, or a plurality of doses of a candidate agent. Candidate agents include small molecules, i.e. drugs, genetic constructs that increase or decrease expression of an RNA of interest, electrical changes, and the like. In some embodiments a panel refers to a system or method utilizing patient-specific cells from two or more distinct conditions, and may be three or more, four or more, five or more, six or more, seven or more genetically distinct conditions.

In some embodiments of the invention, methods are provided for determining the activity of a candidate agent on oligodendrocytes from the hOS, the method comprising contacting the candidate agent with one or a panel of purified neurons, astrocytes, OPSs or oligodendrocyte populations differentiated from induced human pluripotent stem cells (hiPSCs). The cell populations optionally comprise at least one allele encoding a mutation associated or causing a myelinating or demyelinating disease or an oligodendrocyte development disorder; and determining the effect of the agent on morphologic, genetic or functional parameters, including without limitation gene expression profiling. The screening methods may be combined with immune effector cells to determine activity of such immune cells of oligodendrocytes and myelination, or the interaction between oligodendrocytes, astrocytes in hOS and autologous immune cells from patients. Methods of analysis at the single cell level are of particular interest, e.g. myelination assays, single cell gene expression, effect of oligodendrocytes on neurons or astrocytes, and neuronal cell signal transmission, and the like. Candidate agents include immune effector cells, e.g. T cells, microglial cells, macrophages, NK cells, etc., and immune effector proteins, e.g. IFN-γ, TGF-β, cytokines, interferons, etc. and the like, particularly such cells and proteins suspected of involvement in inflammatory demyelinating diseases.

The methods of the invention utilize the natural interactions between neural cells and progenitors in the differentiation of oligodendrocytes and formation of myelin sheaths. In some embodiments, the differentiation from hiPSCs to oligodendrocytes is performed in substantially serum-free medium.

After differentiation in hOS, individual cell types of interest, including and without limitation to oligodendrocytes, can be isolated for various purposes. The cells are harvested at an appropriate stage of development, which may be determined based on the expression of markers and phenotypic characteristics of the desired cell type. Cultures may be empirically tested by immunostaining or gene expression for the presence of the markers of interest, by morphological determination, etc. The cells are optionally enriched before or after the positive selection step by drug selection, panning, density gradient centrifugation, etc. In another embodiment, a negative selection is performed, where the selection is based on expression of one or more of markers found on human ES cells, fibroblasts, neural cells, epithelial cells, and the like. Selection may utilize panning methods, magnetic particle selection, particle sorter selection, and the like.

Various somatic cells find use as a source of hiPSCs; of particular interest are adipose-derived stem cells, fibroblasts, keratinocytes, peripheral blood cells, and the like. The use of hiPSCs from individuals of varying genotypes, particularly genotypes potentially associated with neurologic and psychiatric disorders are of particular interest. The hiPSCs are dissociated as single cells, aggregated in spheroids of specific cell numbers and then grown in suspension; then induced to a neural fate by inhibition of BMP and TGFβ pathways. The spheroids are then moved to medium in the presence of FGF2 and EGF and are patterned with Wnt pathway inhibitors or retinoic acid, as well as activators of the sonic hedgehog pathway. To promote differentiation, the spheroids are changed to medium comprising PDGF-AA, IGF-1, HGF, insulin, BDNF, NT3, cAMP, T3, and biotin. After such culture, the spheroids can be maintained for extended periods of time in neural medium containing insulin, ascorbic acid, cAMP, T3, and biotin in the absence of growth factors, e.g. for periods of 1, 2, 3, 4, 5, 6, 7, 8, 9, 10, 11, 12 months or longer.

These and other objects, advantages, and features of the invention will become apparent to those persons skilled in the art upon reading the details of the subject methods and compositions as more fully described below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following FIGURES.

FIG. 1A-1F.

DETAILED DESCRIPTION OF THE INVENTION

Before the present compositions and methods are described, it is to be understood that this invention is not limited to particular compositions and methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a reprogramming factor polypeptide" includes a plurality of such polypeptides, and reference to "the induced pluripotent stem cells" includes reference to one or more induced pluripotent stem cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "pluripotency" and pluripotent stem cells it is meant that such cells have the ability to differentiate into all types of cells in an organism. The term "induced pluripotent stem cell" encompasses pluripotent cells, that, like embryonic stem cells (ESC), can be cultured over a long period of time while maintaining the ability to differentiate into all types of cells in an organism, but that, unlike ESCs, are derived from differentiated somatic cells, that is, cells that had a narrower, more defined potential and that in the absence of experimental manipulation could not give rise to all types of cells in the organism. hiPSC have a human ESC-like morphology, growing as flat colonies with large nucleo-cytoplasmic ratios, defined borders and prominent nuclei. In addition, hiPSC express several pluripotency markers known by one of ordinary skill in the art, including but not limited to alkaline phosphatase, SSEA3, SSEA4, SOX2, OCT3/4, NANOG, TRA-160, TRA-181, TDGF1, DNMT3B, TERT, and ZFP42. In addition, the hiPSC are capable of forming teratomas. They are capable of forming or contributing to ectoderm, mesoderm, or endoderm tissues in a living organism.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; SOX2; KLF3; c-MYC; NANOG; and LIN-28.

Somatic cells are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector. The somatic cells may be fibroblasts, adipocytes, stromal cells, and the like, as known in the art. Somatic cells or hiPSC can be obtained from cell banks, from normal donors, from individuals having a neurological or psychiatric disease of interest, etc.

Following induction of pluripotency, hiPSC are cultured according to any convenient method, e.g. on irradiated feeder cells and commercially available medium. The hiPSC can be dissociated from feeders by digesting with protease, e.g. accutase, preferably at a concentration and for a period of time sufficient to detach single cells from the plate.

Genes may be introduced into the somatic cells or the hiPSC derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as BCL-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The terms "oligodendrocyte," "oligodendrocyte progenitor cell," etc. can encompass cells of the oligodendrocyte lineage, i.e. neural progenitor cells that ultimately give rise to oligodendrocytes, oligodendrocyte precursor cells, and mature and myelinating oligodendrocytes, which for the purposes of the present invention arise from a non-oligodendrocyte cell by experimental manipulation. Oligodendrocytes can be identified by markers specific for cells of the oligodendrocyte lineage as discussed below. Oligodendrocytes may have functional characteristics, that is, they may have the capacity of myelinating neurons; and the like. An "oligodendrocyte precursor" or "oligodendrocyte progenitor cell" is defined as a cell that is capable of giving rise to progeny that include oligodendrocytes.

Oligodendrocytes are the myelin-forming cells of the central nervous system. An oligodendrocyte extends many processes which contact and repeatedly envelope stretches of axons. Subsequent condensation of these wrapped layers of oligodendrocyte membrane form the myelin sheath. One axon may contain myelin segments from many different oligodendrocytes.

Myelination requires a number of sequential steps in the maturation of the oligodendroglial cell lineage. These steps are accompanied by coordinated changes in the expression of cell surface antigens. Markers of oligodendrocyte progenitor cells include, for example, platelet-derived growth factor α-receptor (PDGFR-α). Other markers of oligodendrocytes include Nestin, proteolipid protein; polysialylated form of neural cell adhesion molecule (NCAM), ganglioside GD3, and carbonic anhydrase II (CA-II). Some markers, such as CA-II, cover all stages of the lineage and are also markers of adult oligodendrocytes. Galactosylceramides and sulfogalactosylceramides are likewise early markers that remain present on the surface of mature oligodendrocytes. Other genes encoding specific myelin proteins are expressed at different stages of oligodendrocyte differentiation and maturation. For example, 2',3'-Cyclic nucleotide-3'-phosphohydrolase (CNP), myelin basic protein (MBP), PLP/DM-20, myelin associated glycoprotein (MAG), and myelin/oligodendrocyte glycoprotein (MOG) genes as well as other minor myelin proteins are all markers for mature oligodendrocytes.

It has been speculated that a number of factors are required for oligodendrocyte maturation and survival. These factors can be tested with the human oligodendrocyte cultures of the present invention. Factors of interest may include PDGF, basic FGF, Insulin-like growth factor I (IGF-I), neurotrophin 3 (NT-3), glial growth factor (GGF), ciliary neurotrophic factor (CNTF), IL-6, transforming growth factor (TGF)-β and IL-2.

The myelin sheath constitutes the most abundant membrane structure in the vertebrate nervous system. The abundance of lipids and low water content in myelin allows for the electrical insulation of axons, and the unique segmental structure of myelinated regions are responsible for the saltatory conduction of nerve impulses. This allows the myelin sheath to support the fast nerve conduction in the relatively thin axons of the vertebrate central nervous system. High-speed conduction, fidelity of transfer signaling on long distances, and space economy are the major advantages conferred to the vertebrate nervous system by the myelin sheath.

The mechanism of myelination and the signals that regulate this complex process may be studied with the cells and culture of the present invention. There are sequential steps involving the migration of oligodendrocytes to axons that are to be myelinated within the 3D spheroids; the adhesion of the oligodendrocyte process to the axon; and the spiraling of the process around the axon, with a predetermined number of myelin sheaths, and the recognition of the space not to be myelinated. Each of these steps can be studied and manipulated in live cells in the proposed invention. Moreover, the interaction between oligodendrocytes and astrocytes during development can be studied in the 3D spheroids presented here. The long culture life of the spheroids also allows for study of myelin plasticity and alterations in these interactions over time.

Migration of oligodendrocytes between brain regions can also be studied in the proposed invention. During brain development, early waves of oligodendrocytes are produced in the subpallium and migrate to the cortex, or pallium. Oligodendrocyte-containing spheroids can be fused with cortical spheroids to model the migrational dynamics, directional cues, and opposing signals that govern oligodendrocyte migration into the cortex. This system can also be used to study diseases in which abnormal oligodendrocyte migration or distribution may play a role. Oligodendrocyte migration is likely to be better preserved in the proposed 3D model as oligodendrocytes in vivo migrate through tissues as opposed to along a flat surface such as in 2D oligodendrocyte models.

In addition to various uses as in vitro cultured cells, the oligodendrocytes may be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether the administered cells or progeny thereof are still present, and may be phenotyped for response to a treatment of interest. Suitability can also be determined in an animal model by assessing the degree of recuperation that ensues after injury or in a disease context as a result of treatment with the differentiating cells of the invention.

Disease relevance. A number of pathologies are associated with oligodendrocyte dysfunction. Inherited myelin diseases in humans, leukodystrophies, may be the result of dysmyelination, hypomyelination, or demyelination. Dysmyelination and hypomyelination are failure to myelinate occurring during fetal life or early infancy, as observed in different forms of Pelizaeus-Merzbacher disease. Demyelination, breakdown of myelin, is characteristic of metabolic leukodystrophies, such as Krabbe's disease, metachromatic leukodystrophy, ALD, Canavan disease, Alexander disease, orthochromatic leukodystrophy, or mitochondrial disorders. Dysmyelination and demyelination can be combined in some forms of leukodystrophies.

Some genetic diseases may give rise to leukoencephalopathies in which demyelination is secondary to vascular, mitochondrial, or neuronal alterations or may be linked to a metabolic disease that may have ubiquitous signs. Cerebral autosomal dominant arteriopathy with subcortical infarcts and leukoencephalopathy (CADASIL) is an autosomal dominant cerebral arteriopathy. MRI evidences multiple subcortical infarcts, with a demyelination of white matter that can be more or less extensive. MELAS (mitochondrial myopathy, encephalopathy, lactic acidosis, strokelike episodes) presents a lactic acidosis with an increase of the lactate-to-pyruvate ratio in serum and CSF. MRI shows white matter modifications are present together with cortical atrophy.

Phenylketonuria can be associated with demyelination. Abnormalities of intermediary metabolism may also cause demyelination. Some neuronal genetic diseases can affect myelin (GM2 gangliosidoses, Wilson's disease, and degenerative diseases of CNS).

Breakdown of the blood-brain barrier is a primary event in pathological manifestations of demyelinating disease of the CNS, such as multiple sclerosis (MS), demyelinating forms of EAE, and virus-induced demyelination. T cells play a pivotal role in this process. Access of activated T cells to the CNS may be responsible for release by inflammatory cells, macrophages, and microglia and of proinflammatory cytokines, such as TNF-α and interferon-γ.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," are used interchangeably herein and refer to any mammalian subject for whom diagnosis, treatment, or therapy is desired, particularly humans.

METHODS OF THE INVENTION

Methods are provided for the obtention and use of in vitro cell cultures of human oligodendro-spheroids (hOS) and cells comprised therein, specifically including oligodendrocytes and neurons, where the cells are differentiated from induced human pluripotent stem cells (hiPSC). In some embodiments the hiPSC are derived from somatic cells obtained from neurologically normal individuals. In other embodiments the hiPSC are derived from somatic cells obtained from an individual comprising at least one allele encoding a mutation associated with a neural disease, including without limitation the myelination associated diseases described above. In some embodiments a panel of such oligodendrocytes are provided, where the panel includes two or more genetically different oligodendrocytes. In some embodiments a panel of such oligodendrocytes are provided, where the oligodendrocytes are subjected to a plurality of candidate agents or other therapeutic intervention, or a plurality of doses of a candidate agent or other therapeutic intervention. Candidate agents include without limitation small molecules, i.e. drugs, genetic constructs that increase or decrease expression of an RNA of interest, electrical changes, and the like.

Methods are also provided for determining the activity of a candidate agent on a disease-relevant cell, the method comprising contacting the candidate agent with one or a panel of cells differentiated from human pluripotent stem cells, e.g. differentiated from hESC or from hiPSC, where the pluripotent stem cells optionally comprise at least one allele encoding a mutation associated with a neural disease; and determining the effect of the agent on morphologic, genetic or functional parameters, including without limitation gene expression profiling. In addition to genetic disease models, these methods can be applied to environmental manipulations that influence oligodendrocyte maturation and myelination, including but not limited to alterations in oxygen tension, temperature, and applied force.

Generation of human oligodendro-spheroids (hOS) and cells comprised therein, including, for example neural progenitors, oligodendrocyte progenitor cells (OPCs), astrocytes, myelinating oligodendroyctes and neurons from somatic cells utilizes a multi-step process. Initially, hiPSC can be obtained from any convenient source, or can be generated from somatic cells using art-recognized methods. The hiPSC are dissociated from feeders and grown in suspension culture in the absence of FGF2, preferably when dissociated as single cells. In certain embodiments the culture are feeder layer free, e.g. when grown on vitronectin coated vessels, and the hiPSC are dissociated as a single cell suspension and aggregated in spheroids of specific sizes. The culture may further be free on non-human components, i.e. xeno-free. Suspension growth optionally includes in the culture medium an effective dose of a selective Rho-associated kinase (ROCK) inhibitor for the initial period of culture, for up to about 6 hours, about 12 hours, about 18 hours, about 24 hours, about 36 hours, about 48 hours, (see, for example, Watanabe et al. (2007) Nature Biotechnology 25:681 686). Inhibitors useful for such purpose include, without limitation, Y-27632; Thiazovivin (Cell Res, 2013, 23(10):1187-200; Fasudil (HA-1077) HCI (J Clin Invest, 2014, 124(9):3757-66); GSK429286A (Proc Natl Acad Sci USA, 2014, 111(12):E1140-8); RKI-1447; AT13148; etc.

The suspension culture of hiPSC is then induced to a neural fate. This culture may be feeder—free. For neural induction, an effective dose of an inhibitor of BMP, and of TGFβ pathways is added to the medium, for a period at least about 2 days, at least about 3 days, at least about 4 days, at least about 5 days, and up to about 10 days, up to about 9 days, up to about 8 days, up to about 7 days, up to about 6 days, up to about 5 days. For example, dorsomorphin (DM) can be added at an effective dose of at least about 0.1 μM, at least about 1 μM, at least about 5 μM, at least about 10 μM, at least about 50 μM, up to about 100 μM concentration, which inhibits bone morphogenetic protein (BMP) type I receptors (ALK2, ALK3 and ALK6). Other useful BMP inhibitors include, without limitation, A 83-01; DMH-1; K 02288; ML 347; SB 505124; etc. SB-431542 can be added at an effective dose of at least about 0.1 μM, at least about 1 μM, at least about 5 μM, at least about 10 μM, at least about 50 μM, up to about 100 μM concentration, which inhibits TGFβ signaling but has no effect on BMP signaling. Other useful inhibitors of TGFβ include, without limitation, LDN-193189 (J Clin Invest, 2015, 125(2):796-808); Galunisertib (LY2157299) (Cancer Res, 2014, 74(21):5963-77); LY2109761 (Toxicology, 2014, 326C:9-17); SB525334 (Cell Signal, 2014, 26(12):3027-35); SD-208; EW-7197; Kartogenin; DMH1; LDN-212854; ML347; LDN-193189 HCI (Proc Natl Acad Sci USA, 2013, 110(52):E5039-48); SB505124; Pirfenidone (Histochem Cell Biol, 2014, 10.1007/s00418-014-1223-0); RepSox; K02288; Hesperetin; GW788388; LY364947, etc.

An effective dose of a Wnt inhibitor may be included in the culture medium beginning at day 2, 3, 4, 5, 6 or 7, for example at a concentration of from about 0.1 μM to about 100 μM, and may be from about 1 μM to about 25 μM, depending on the activity of the inhibitor that is selected. Exemplary inhibitors include, without limitation, XAV-939 selectively inhibits Wnt/β-catenin-mediated transcription through tankyrase1/2 inhibition with IC50 of 11 nM/4 nM in cell-free assays; ICG-001 antagonizes Wnt/β-catenin/TCF-mediated transcription and specifically binds to element-binding protein (CBP) with IC50 of 3 μM; IWR-1-endo is a Wnt pathway inhibitor with IC50 of 180 nM in L-cells expressing Wnt3A, induces Axin2 protein levels and promotes β-catenin phosphorylation by stabilizing Axin-scaffolded destruction complexes; Wnt-C59 (C59) is a PORCN inhibitor for Wnt3A-mediated activation of a multimerized TCF-binding site driving luciferase with IC50 of 74 pM in HEK293 cells; LGK-974 is a potent and specific PORCN inhibitor, and inhibits Wnt signaling with IC50 of 0.4 nM in TM3 cells; KY02111 promotes differentiation of hPSCs to cardiomyocytes by inhibiting Wnt signaling, may act downstream of APC and GSK3β; IWP-2 is an inhibitor of Wnt processing and secretion with IC50 of 27 nM in a cell-free assay, selective blockage of Porcn-mediated Wnt palmitoylation, does not affect Wnt/β-catenin in general and displays no effect against Wnt-stimulated cellular responses; IWP-L6 is a highly potent Porcn inhibitor with EC50 of 0.5 nM; WIKI4 is a novel Tankyrase inhibitor with IC50 of 15 nM for TNKS2, and leads to inhibition of Wnt/beta-catenin signaling; FH535 is a Wnt/β-catenin signaling inhibitor and also a dual PPARγ and PPARδ antagonist. Instead of a Wnt inhibitor, retinoic acid may be included in the culture media at concentrations ranging from 10 nM to 1 μM.

Agonists of the sonic hedgehog pathway may also be added starting at day 10, 11, 12, 13, 14, or 15. Potential agonists include SAG and purmorphamine, used at concentrations ranging from to 100 nm to 10 μM.

After about 5 days, about 6 days, about 7 days, about 8 days, about 9 days, about 10 days in suspension culture, the floating spheroids are moved to neural media to differentiate neural progenitors. The media is supplemented with an effective dose of FGF2 and EGF. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml.

To promote differentiation of early progenitors into oligodendrocytes, after about 1 week, about 2 weeks, about 3 weeks, about 4 weeks after FGF2/EGF exposure the neural medium is changed to replace the FGF2, EGF, IWP-2, and SAG with an effective dose of PDGF-AA, IGF-1, HGF, BDNF and NT3. The growth factors can be provided at a concentration for each of at least about 0.5 ng/ml, at least about 1 ng/ml, at least about 5 ng/ml, at least about 10 ng/ml, at least about 20 ng/ml, up to about 500 ng/ml, up to about 250 ng/ml, up to about 100 ng/ml. The medium may further comprise, for example, insulin, T3, cAMP analog, biotin, etc., for insulin at a concentration of up to about 50 µg/ml, up to about 25 µg/ml.

After about 4 weeks, about 5 weeks, about 6 weeks, about 7 weeks after exposure to differentiation factors, the spheres can be maintained for extended periods of time in neural medium in the absence of growth factors, e.g. for periods of 1, 2, 3, 4, 5, 6, 7, 8, 9, 10, 11, 12 months or longer. The neural medium may comprise ascorbic acid, 25 µg/mL insulin, 1 µM cAMP analog, 60 ng/mL T3, and 100 ng/mL biotin with media changes taking place every 4-5 days.

Populations of cells can be isolated from the spheres by any convenient method, including flow cytometry, magnetic immunoselection, immunopanning, etc. Conveniently, PDGFR and/or MBP are used of positive selection markers for oligodendrocyte progenitors and oligodendrocytes, respectively. The cells thus isolated can be resuspended in an acceptable medium and maintained in culture, frozen, analyzed for parameters of interest; transplanted into a human or animal model; and the like. Populations of oligodendrocyte progenitor cells or oligodendrocytes are of interest, for example, in methods of remyelination of CNS neurons, e.g. in regrowth of neurons following traumatic damage, in therapeutic treatment of demyelinating diseases such as multiple sclerosis, and the like, where an effective dose of cells is provided to a patient in need thereof.

Screening Assays

In screening assays for the small molecules, the effect of adding a candidate agent to cells in culture is tested with a panel of cells and cellular environments, where the cellular environment includes one or more of: electrical stimulation including alterations in ionicity, stimulation with a candidate agent of interest, contact with other cells including without limitation neurons and neural progenitors, immune effector cells such as T cells, microglial cells, macrophages, etc. and the like, and where panels of oligodendrocytes may vary in genotype, in prior exposure to an environment of interest, in the dose of agent that is provided, etc. Usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphological, functional and genetic changes.

In the screening assays for genetic agents, polynucleotides can be added to one or more of the cells in a panel in order to alter the genetic composition of the cell. The output parameters are monitored to determine whether there is a change in phenotype. In this way, genetic sequences are identified that encode or affect expression of proteins in pathways of interest. The results can be entered into a data processor to provide a screening results dataset. Algorithms are used for the comparison and analysis of screening results obtained under different conditions.

Methods of analysis at the single cell level are of particular interest, e.g. as described above: atomic force microscopy, single cell gene expression, single cell RNA sequencing, calcium imaging, flow cytometry, myelination, electron microscopy, live imaging, and the like. Various parameters can be measured to determine the effect of a drug or treatment on the oligodendrocytes.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc., including various myelin components as disclosed herein. Cell surface, myelin, and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:I to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an anti-sense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Agents are screened for biological activity by adding the agent to at least one and usually a plurality of cells, in one or in a plurality of environmental conditions, e.g. following stimulation with a β-adrenergic agonist, following electric or mechanical stimulation, etc. The change in parameter readout in response to the agent is measured, desirably normalized, and the resulting screening results may then be evaluated by comparison to reference screening results, e.g. with cells having other mutations of interest, normal oligodendrocytes, oligodendrocytes derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

The comparison of screening results obtained from a test compound, and a reference screening results(s) is accomplished by the use of suitable deduction protocols, AI systems, statistical comparisons, etc. Preferably, the screening results is compared with a database of reference screening results. A database of reference screening results can be compiled. These databases may include reference results from panels that include known agents or combinations of agents, as well as references from the analysis of cells treated under environmental conditions in which single or multiple environmental conditions or parameters are removed or specifically altered. Reference results may also be generated from panels containing cells with genetic constructs that selectively target or modulate specific cellular pathways.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

For convenience, the systems of the subject invention may be provided in kits. The kits could include the cells to be used, which may be frozen, refrigerated or treated in some other manner to maintain viability, reagents for measuring the parameters, and software for preparing the screening results. The software will receive the results and perform analysis and can include reference data. The software can also normalize the results with the results from a control culture. The composition may optionally be packaged in a suitable container with written instructions for a desired purpose, such as screening methods, and the like.

For further elaboration of general techniques useful in the practice of this invention, the practitioner can refer to standard textbooks and reviews in cell biology, tissue culture, embryology, and neurobiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

Previous methods to generate human oligodendrocytes and model the process of myelination in vitro have been performed in two-dimensional (2D) cultures. In these protocols, myelination is studied as the wrapping of oligodendrocyte processes around synthetic nanopillars. These methods do not allow for the study of myelination as it occurs in the human brain as a three-dimensional process. Alternatively, human stem cell-derived oligodendrocytes have been transplanted into rodents, however it is not known to what extent the mouse environment influences human oligodendrocyte biology and myelination, and these methods are laborious and not allowing for high-throughput screenings. The method described below is the first to generate in vitro myelinating oligodendrocytes in three-dimensional (3D) cultures derived solely from human hiPSCs or hESC, allowing the study of human myelination in healthy and disease conditions in vitro.

hiPSC maintenance and aggregation. Human induced pluripotent stem cell (hiPSC) lines were cultured on tissue culture-treated plates coated with vitronectin (0.5 µg/cm$^2$) in iPSC media (complete E8 media containing 100 U/mL penicillin and 100 µg/mL streptomycin). To form floating aggregates, Aggrewell plates were first prepared by centrifuging 500 µL of hiPSC media plus the ROCK inhibitor Y-27632 (10 nM) for 5 minutes at 2,000 g. hiPSCs were pretreated with Y-27632 for 1 hour then dissociated by treatment with prewarmed accutase for 5-7 minutes. Once dissociated, hiPSCs were collected and diluted in hiPSC media then counted. Aliquots of 3 million hiPSCs were transferred to 15 mL falcon tubes, centrifuged at 2,000 g for 5 minutes, and then resuspended in 1.5 mL of hiPSC media with Y-27632. The 3 million cell suspensions were then added to individual wells of the prepared Aggrewell plate, and the plates were centrifuged for 3 minutes at 100 g. Aggrewell plates were then stored in a 37 C incubator with 5% $CO_2$ overnight.

The following day, hiPSC aggregates were flushed from the Aggrewells by pipetting with a P-1000 pipet using a cut tip. Dislodged aggregates were strained using a 40 µm cell filter and transferred to 100 mm ultra-low attachment tissue culture dishes containing E6 media with 100 U/mL penicillin and 100 µg/mL streptomycin.

Neural induction and promotion of oligodendrogenesis. For neural induction, dorsomorphin (5 µM) and SB-431542 (10 µM) were added daily for the first 6 days. Two variations of spheroids were generated, in which some were exposed to all-trans retinoic acid (RA, 100 nM) daily beginning on the third day, and others to the Wnt pathway inhibitor IWP-2 (5 µM) beginning on the fourth day. On the sixth day in suspension, the floating spheroids were moved to neural medium (NM) containing DMEM/F12, N-2 supplement, B-27 serum substitute without vitamin A, GlutaMax (1:100), MEM Non-Essential Amino Acid Solution (1:100), 0.1 nM β-mercaptoethanol, 100 U/mL penicillin, and 100 µg/mL streptomycin. The NM was also supplemented with 20 ng/ml FGF2 and 20 ng/ml EGF for 19 days with daily medium change in the first 10 days, and every other day for the subsequent 9 days. On day 11, the smoothened agonist SAG (1 µM) was also added daily to the media. To promote differentiation of the neural progenitors into oligodendrocytes, FGF2, EGF, IWP-2, RA, and SAG were removed and 10 ng/mL PDGF-AA, 10 ng/mL IGF-1, 5 ng/mL HGF, 25 µg/mL insulin, 1 µM cAMP analog, 60 ng/mL T3, 100 ng/mL biotin, 20 ng/ml BDNF and 20 ng/ml NT3 were added to the NM media starting at day 25. Media changes took place every other day from day 25 to day 43. From day 43 onwards, spheroids were cultured in NM with 20 µg/mL ascorbic acid, 25 µg/mL insulin, 1 µM cAMP analog, 60 ng/mL T3, and 100 ng/mL biotin with media changes taking place every 4-5 days.

Figure 1A:
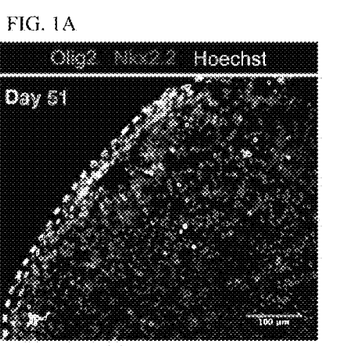
FIG. 1A Oligodendrocyte progenitor cells and mature oligodendrocytes produced in 3D human iPSC-derived oligo-spheroids (hOS). NKX2.2/OLIG2$^+$ oligodendrocyte progenitor cells are present in fixed sections of 51-day-old hOS.
Figure 1B:
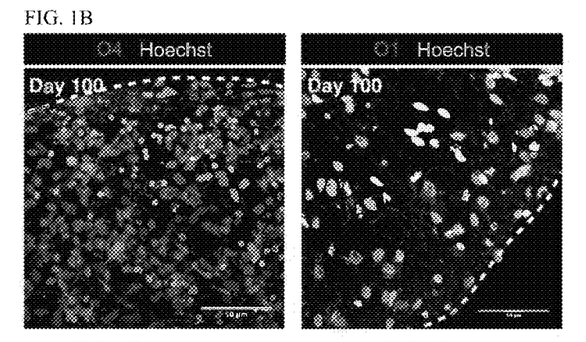
FIG. 1B Examples of O4$^+$ and O1$^+$ oligodendrocytes in fixed sections of 100-day-old hOS.

Results:

FIGS. 1a-1b. Derivation of oligodendrocytes in 3D culture. After 51 days in culture, spheroids were fixed overnight in 4% PFA. The spheroids were embedded in OCT, sectioned, and immunoflourescently labeled using antibodies against NKX2.2 and OLIG2, markers that together identify oligodendrocyte progenitor cells. The same procedure was used to fix and prepare sections from 100-day-old hOS, which were then immunoflourescently labeled with O4, a surface marker for young and mature oligodendrocytes, and O1, a surface marker for mature oligodendrocytes. The presence of NKX2.2/OLIG2$^+$ cells and multipolar O4$^+$ and O1$^+$ cells suggests that both oligodendrocyte progenitor cells and mature oligodendrocytes are present in human spheroids derived by the described method.

Figure 1C:
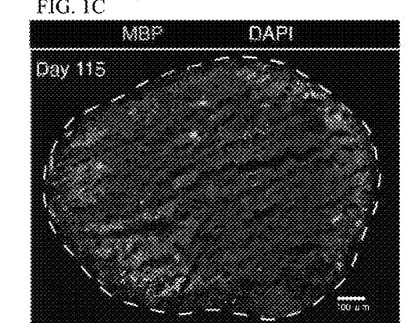
FIG. 1C Immunofluorescent labeling demonstrating the distribution of MBP$^+$ mature oligodendrocytes in fixed sections of 115-day-old hOS.
Figure 1D:
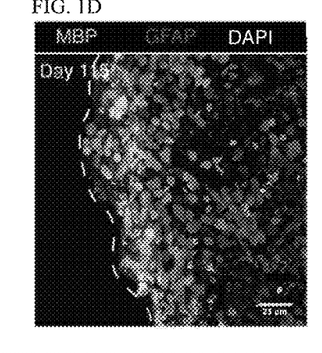
FIG. 1D Examples of MBP$^+$ oligodendrocyte processes and GFAP+ astrocyte processes physically interacting in fixed sections in 115-day-old hOS.
Figure 1E:
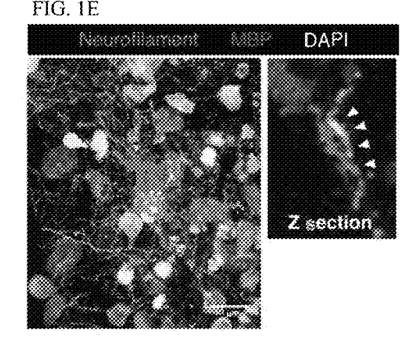
FIG. 1E Example of MBP$^+$ oligodendrocyte processes wrapping Neurofilament+ axons in fixed sections of 115-day-old hOS.

FIG. 1c-e. Interactions between cell types in 3D culture. Sections were prepared from 115-day-old hOS and labeled with antibodies against MBP—a protein involved in the formation of myelin and marker of mature oligodendrocytes, GFAP—a marker for astrocytes, and Neurofilament—a marker for axons. Overlap between MBP$^+$ and GFAP$^+$ processes indicate oligodendrocyte-astrocyte interaction. Wrapping of MBP$^+$ processes around Neurofilament$^+$ processes suggest that oligodendrocytes are wrapping axons in 115-day-old hOS.

Figure 1F:
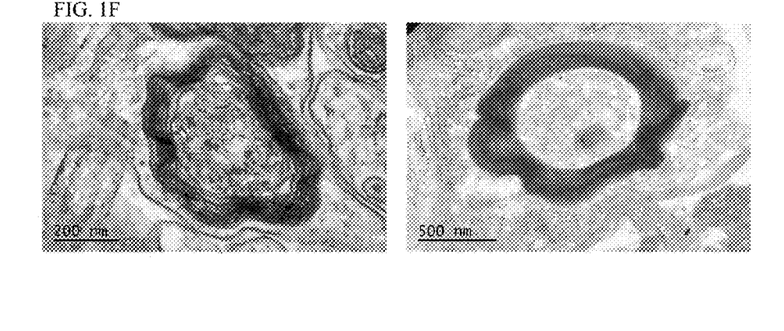
FIG. 1F Examples of myelination in human iPSC-derived hOS. Transmission electron microscopy images of myelinated axons were taken at day 100 in vitro.

FIG. 1f. Myelination in human hiPSC-derived 3D culture (hOS). After 100 days in culture, spheroids derived by the described method were fixed and processed for transmission electron microscopy. The presence of ring-like layers surrounding axons is consistent with myelination.

Significance and applications. Myelination is essential to normal brain function, and aberrations in myelination underlie numerous neurological disorders. The human neural 3D spheroids described in this method are the first to contain myelinating oligodendrocytes and can be used to systematically study the process of myelination in health and disease. This method is especially amenable to disease modeling as the hiPSCs utilized in this protocol can be reprogrammed directly from the skin cells of patients with demyelinating disorders. Additionally, due to the scalability of the method, these cultures can also be used for drug screening to identify compounds that influence myelination both in healthy and disease-specific contexts. Moreover, this is also the first system to allow for the study of key cell-cell interaction in human development, between neurons and oligodendrocytes, oligodendrocyte and astrocytes, etc. Finally, the oligodendrocytes derived in these cultures can serve as a source of cells for transplantation in future treatments of demyelinating disorders.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for producing a 3-dimensional culture of human interacting myelinating oligodendrocytes, myelinated neurons and astrocytes, the method comprising:
   (i) inducing human pluripotent human stem cells in suspension culture to a neural fate by culturing intact colonies or aggregates of single cells of the pluripotent stem cells for a period of from 2 to 10 days in medium comprising an effective dose of an inhibitor of BMP and an inhibitor of TGFβ to generate a spheroid of cells;
   (ii) differentiating the spheroid of pluripotent human stem cells to a spheroid of neural progenitors by culturing in suspension culture for a period of from 1 to 4 weeks in medium comprising fibroblast growth factor 2 (FGF2) and epidermal growth factor (EGF);
   (iii) differentiating the spheroid of neural progenitors into a spheroid (hOS) comprising interacting human oligodendrocytes, human neurons, and human astrocytes by culturing in neural media lacking FGF2 and EGF and comprising an effective dose of PDGF-AA, IGF-1, HGF, BDNF, NT3, insulin, cAMP, T3, and biotin;
   (iv) maintaining the hOS spheroid for one month or longer in neural medium to derive 3-dimensional cultures that comprise interacting myelinating oligodendrocytes, myelinated neurons and astrocytes.

2. The method of claim 1, wherein the cells comprise at least one allele associated with a myelin disorder.

3. The method of any of claim 1, wherein the pluripotent stem cells are induced pluripotent stem cells.

4. The method of claim 1, wherein the inhibitor of BMP is dorsomorphin and the inhibitor of TGFβ is SB-431542.

5. The method of claim 4, wherein the suspension culture of (i) is feeder layer free.

6. The method of claim 1, wherein the medium in (i) further comprises an effective dose of an inhibitor of wnt, beginning day 2 of culture.

7. The method of claim 1, further comprising culturing the spheroids in step (i) with sonic hedgehog pathway agonists and retinoic acid; or with sonic hedgehog pathway agonists and Wnt inhibitors.

8. The method of claim 1, wherein the neural medium in (iv) is lacking growth factors but including ascorbic acid, insulin, cAMP, T3, and biotin.

9. The method of claim 8, further comprising isolating oligodendrocytes from an oligodendro-spheroid by flow cytometry, magnetic immunoselection, or immunopanning.

10. The method of claim 9, wherein isolated oligodendrocytes are exposed to a candidate agent or treatment of interest.

11. The method of claim 10, wherein the oligodendrocytes are combined with neurons or neuronal progenitor cells or glial cells.

12. The method of claim 10, further comprising the step of determining the effect of the agent on morphologic, genetic or functional parameters.

13. The method of claim 12, wherein the candidate agent is an immune effector cell or an immune modulatory agent.

14. The method of claim 10, wherein a panel of oligodendrocytes comprising at least two oligodendrocytes having differing genotypes are isolated and contacted with the candidate agent or treatment of interest.

15. The method of claim 10, wherein a panel of oligodendrocytes comprising at least two oligodendrocytes under differing culture conditions are isolated and contacted with the candidate agent or treatment of interest.

16. The method of claim 10, wherein the isolated oligodendrocytes comprise at least one allele associated with a neural disease.

* * * * *

UNITED STATES PATENT AND TRADEMARK OFFICE
CERTIFICATE OF CORRECTION

PATENT NO. : 11,760,974 B2
APPLICATION NO. : 15/953197
DATED : September 19, 2023
INVENTOR(S) : Rebecca Marton et al.

Page 1 of 1

It is certified that error appears in the above-identified patent and that said Letters Patent is hereby corrected as shown below:

In the Claims

Claim 1:
Column 20, Lines 2 and 8, please delete the word "from".

Column 20, Line 12, please delete "spheroid", and replace it with --human oligodendro-spheroid--.

Signed and Sealed this
Second Day of January, 2024

Katherine Kelly Vidal
*Director of the United States Patent and Trademark Office*